United States Patent [19]

Biringer et al.

[11] Patent Number: 5,124,152
[45] Date of Patent: Jun. 23, 1992

[54] PARENTERAL FORMULATION OF METOLAZONE

[75] Inventors: Jennifer M. Biringer, Rochester; Martin L. Eichman, Fairport, both of N.Y.

[73] Assignee: Fisons Corporation, Rochester, N.Y.

[21] Appl. No.: 638,292

[22] Filed: Jan. 7, 1991

[51] Int. Cl.$^5$ .................. C07D 239/72; A01N 43/42; A61K 31/47
[52] U.S. Cl. .................. 424/422; 514/312; 514/869; 544/231; 544/288
[58] Field of Search ............... 424/422; 544/231, 288; 514/312, 869

[56] References Cited

U.S. PATENT DOCUMENTS 4,472,380 9/1984 Harris et al. ............... 514/2

OTHER PUBLICATIONS

A. I. Cohen, et al., Physiological Disposition of a New Diuretic, $^{14}$C-Metolazone, in Dogs. (J. Pharmaceutical Sciences (1973), vol. 62, 931–936).

E. J. Belair, The Renal Pharmacology of Metolazone, 2-Methyl-3-o-tolyl-6-sulfamyl-7-chloro-1,2,3,4-tetrahydro-4-quinazolinone, (Research Communications in Chemical Pathology and Pharmacology, (1971), vol. 2, No. 1).

Primary Examiner—Thurman K. Page
Assistant Examiner—C. Azpuru
Attorney, Agent, or Firm—McAulay Fisher Nissen Goldberg & Kiel

[57] ABSTRACT

There are described pharmaceutical compositions comprising aqueous solutions of 7 c l r - ,2,3,4-tetrahydro-2-methyl-3-2-methylphenyl)-4-oxo-6-quinazolinesulfonamide. ethanol and a cosolvent selected from propylene glycol or polyethylene glycols suitable for parenteral administration to a patent suffering from refractory edema.

8 Claims, 1 Drawing Sheet

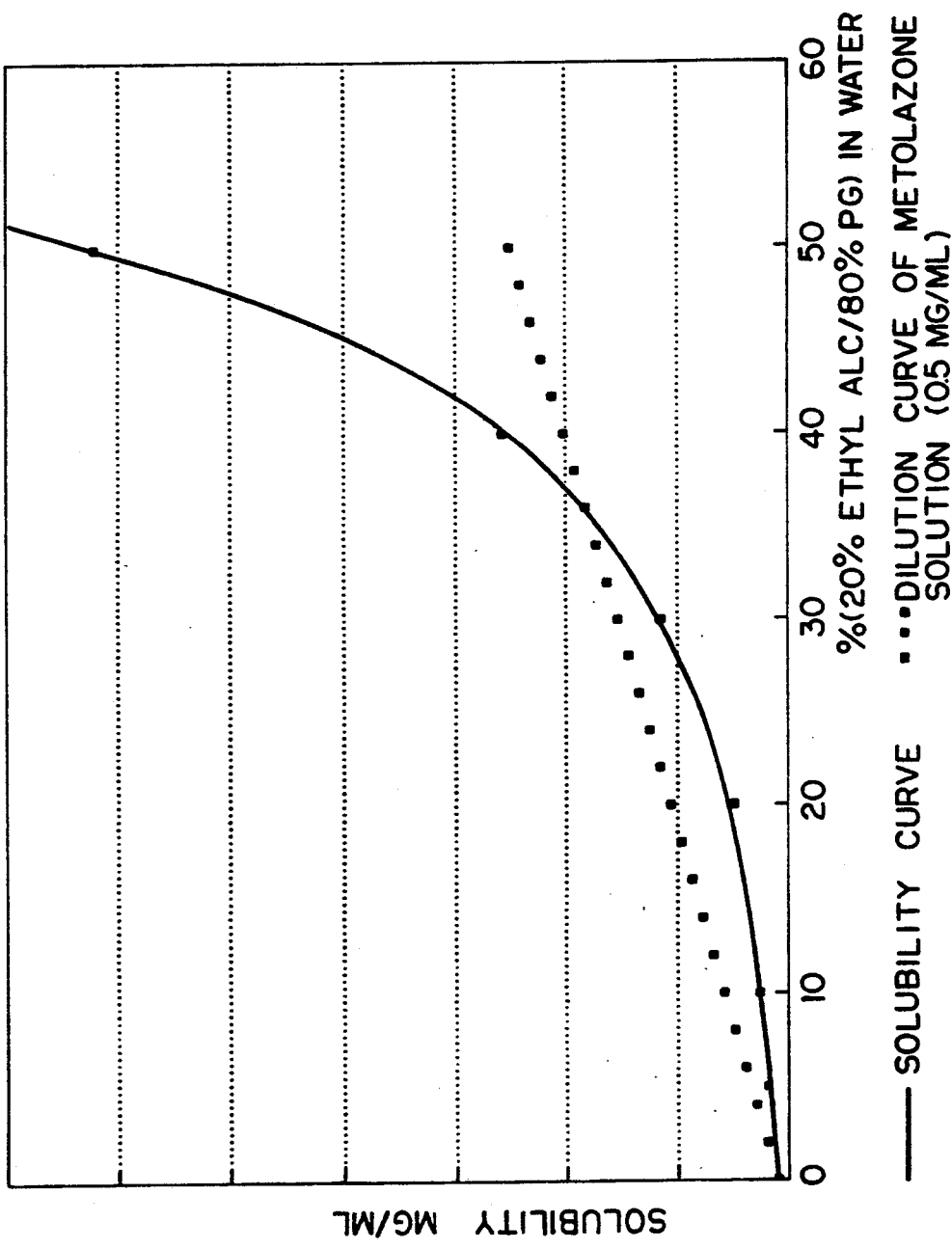
FIG. 1 METOLAZONE SOLUBILITY IN VARIOUS ETHYL/ALCOHOL (95%)/PROPYLENE GLYCOL-WATER SOLUTIONS

PARENTERAL FORMULATION OF METOLAZONE

This invention relates to novel formulations of metolazone, an antihypertensive and diuretic drug substance, comprising aqueous ethanolic solutions suitable for parenteral administration.

BACKGROUND

Metolazone, 7-chloro-1,2,3,4-tetrahydro-2-methyl-3-(2-methylphenyl)-4-oxo-6-quinazolinesulfonamide, is a potent antihypertensive and diuretic drug which is widely available in oral dosage forms. In hospital and other critical care situations it is desirable to have available an injectable form of the drug, for example, in the case of refractory edema or renal failure. Aqueous solutions are preferred for parenteral dosage forms, however, metolazone is virtually insoluble in water (0.02 mg/mL) and thus achieving an effective concentration in a volume of water suitable for parenteral administration is not practical.

Drug substances which are insoluble in water may be solubilized by alternative methods. Where the drug substance possesses acidic or basic functional groups salt formation with pharmaceutically acceptable bases or acids is possible. Salts are usually more soluble in water than the free drug substance because of their ionic nature. Metolazone possesses an acidic sulfonamide group capable of forming salts with strong bases, for example, alkali hydroxides such as sodium or potassium hydroxides. The sodium salt of metolazone is quite soluble in aqueous sodium hydroxide solutions, however a pH of 11.0 is required to maintain solution. Parenteral administration of solutions at pH 11 frequently causes irritation at the site of injection which may be due to the high pH or to precipitation of the drug. Unfortunately the stability of metolazone in such an aqueous solution is poor and degradation of the metolazone is observed. A parenteral formulation of metolazone comprising a lyophilized solid prepared from the sodium salt of metolazone and sodium hydroxide is more stable but reconstitution of the solid with water still requires a pH of about 11. Reconstitution of drug compositions requires extra steps, is prone to error and is generally considered inconvenient by physicians and nurses.

Ready made solutions are more desirable as parenteral formulations and solutions of water-insoluble drug substances in suitable solvents or mixtures of such solvents may provide an alternative method of obtaining an acceptable parenteral formulation, especially if the problems of irritation and/or precipitation at the site of injection are also overcome. It is usually desirable to administer as low a total volume of the injectable solution as possible in order to minimise the side effects due to the solvent. Consideration must also be given to the risk of precipitation of the drug when the solution is diluted in realistic proportions with other infusion solutions. Precipitation upon intravenous injection can result in erratic or reduced drug bioavailability, pain upon injection and/or phlebitis.

Among the cosolvent mixtures which are acceptable for pharmaceutical parenteral formulations are aqueous mixtures with one or more of propylene glycol, ethanol, benzyl alclohol, polyethylene glycols and castor oil in various proportions. Ethanol may be used in the form of absolute alcohol or aqueous ethanol (95%). Polyethylene glycol 300 and polyethylene glycol 400 are preferred liquid forms of polyethylene glycol.

Important criteria for a cosolvent parenteral formulation of metolazone are that (a) the solvent mixture be acceptable, (b) the volume be minimized so that the daily administration does not exceed a practical volume of about 20 mL, (c) precipitation of the drug substance at the site of injection be negligible.

Precipitation at the site of injection is related to the solubility of the drug in the aqueous biological fluids. The rate of administration of the solution of the drug substance determines the degree of dilution in biological fluids and whether the solubility of the drug in the mixture of fluids will be exceeded. Normally one would expect that if the concentration of the drug at the site of injection exceeds the solubilty of the drug in the biological fluid precipitation would occur.

BRIEF DESCRIPTION OF THE DRAWINGS

FIG. 1 is a graph depicting a comparison of the solubility of metolazone in water and organic solvents.

DETAILED DESCRIPTION

Suprisingly it has been discovered that certain metolazone solutions can be diluted with water without precipitation even though the apparent solubility level of metolazone in water is exceeded. Thus unexpectedly formulations of metolazone comprising aqueous mixtures of ethanol with propylene glycol or polyethylene glycols have been discovered which on further dilution with water show a negligible tendency to form a precipitate even though the apparent solubility level of metolazone in water is exceeded. Such formulations are thus suitable for parenteral administration of metolazone without causing irritation.

According to the invention, we provide a pharmaceutical composition comprising an aqueous solution of from 0.1-8 mg/mL metolazone, 5-15% w/v ethanol (95%), 0-3% benzyl alcohol v/v and a cosolvent selected from 30-65% w/v propylene glycol, 25-50% v/v polyethylene glycol 300 or 25-50% v/v polyethylene glycol 400.

Preferred aqueous solutions are those in which;

metolazone is present in the amount of 0.25-5 mg/mL, more preferably 0.5 mg/mL;

propylene glycol is present in the amount of 30-50% w/v, more preferably 40% w/v;

ethanol (95%) is present in the amount of 5-10% w/v, more preferably 10% w/v;

polyethylene glycol 300 is present in the amount of 30-50% v/v, more preferably 40% v/v;

polyethylene glycol 400 is present in the amount of 30-50% v/v, more preferably 40% v/v; and benzyl alcohol is present in the amount of 1-2% v/v, more preferably 1-1.5% v/v Metolazone may be administered to a patient in need of parenteral treatment in a daily dose of 1 to 100 mg. A more desirable daily dose would be from 1-10 mg. With the most preferred solution containing 0.5 mg/mL and a daily dose of 10 mg the total volume administered in a day would be 20 mL.

The solubility of metolazone in various ethyl alcohol (95%)/propylene glycol/water solutions was studied under equilibrium conditions. It was determined from FIG. 1 that metolazone exceeds its saturation level when the broken line is above the solubility curve. At these concentrations, precipitation would be expected at equilibrium. For example, from the results shown in FIG. I, dilution of 5 mL of product containing 2.5 mg of metolazone in an 10% w/v ethanol (95%), 40% w/v propylene glycol and 50% w/v water solution with more than 1.5 mL of water would exceed the solubility of the drug and precipitation of the drug would be expected. Expressed in a different way in order to maintain solution of metolazone a 5 mL vial would have to be diluted with 220 mL or more of water.

The tendency of a drug to precipitate upon dilution in a stream of biological fluid can be studied according to the method of Yalkowsky et al (J. Pharm. Sci. 1983, 72, 1014–1017) To simulate biolgical fluids normal saline (0.9% sodium chloride solution) is pumped by a peristaltic pump at a flow rate of 30 mL/min. through a 1.0 mm diameter tubing. At a distance of 30 cm from the flow cell a cosolvent solution of the drug, corresponding to the pharmaceutical dosage form, is injected by syringe at different injection rates. Precipitation of the drug is detected by comparing the absorbance versus time spectrum of the drug formulation with placebo at 400 nm. Injection rates of 10, 8, 6, 4, 3, 2 and 1 mL/min were achieved by injecting 1.0 mL of drug solution over periods of 6.0, 7.5, 10, 15, 20, 30 and 60 sec. respectively.

A cosolvent solution of 10% w/v ethanol (95%), 40% w/v propylene glycol and 50% w/v water containing metolazone (0.5 mg/mL) was injected. As the injection rate was increased metolazone showed no tendency to precipitate. It is apparent that even at the slowest rate of injection the equilibrium concentration of metolazone would have been exceeded.

In contrast when an aqueous solution of diazepam (5 mg/mL) in 10% w/v ethanol (95%), 40% w/v propylene glycol, 1.5% w/v benzyl alcohol, 4% w/v sodium benzoate and 1% w/v benzoic acid which is comparable to the commercial parenteral solution, was injected in a similar manner precipitation readily occurred as the injection rate was increased. Diazepam has been reported to be irritating and to precipitate upon intravenous injection.

The invention is illustrated but in no way limited by the following Examples:

EXAMPLE 1 metolazone: 0.5 g
ethanol (95%): 100.0 g
propylene glycol: 400.0 g
water q.s. to: 1.0 L

EXAMPLE 2 metolazone: 1.17 mg/mL
ethanol (95%): 10% v/v
propylene glycol: 40% v/v
water: 50% v/v

EXAMPLE 3 metolazone: 1.26 mg/mL
ethanol (95%): 10% w/v
propylene glycol: 40% w/v
water: 50% w/v

EXAMPLE 4 metolazone: 0.57 mg/mL
ethanol (95%): 10% w/v
propylene glycol: 30% w/v
water: 60% w/v

EXAMPLE 5 metolazone: 0.38 mg/mL
ethanol (95%): 6.7% w/v
propylene glycol: 30% w/v
water: 63.3% w/v

EXAMPLE 6 metolazone: 3.09 mg/mL
ethanol (95%): 10% v/v
polyethylene glycol 300: 40% v/v
water: 50% v/v

EXAMPLE 7 metolazone: 2.60 mg/mL
ethanol (95%): 10% v/v
polyethylene glycol 400: 40% v/v
water: 50% v/v

EXAMPLE 8 metolazone: 1.50 mg/mL
ethanol (95%): 10% v/v
polyethylene glycol 400: 30% v/v
benzyl alcohol: 1% v/v
water: 59% v/v

EXAMPLE 9 metolazone: 4.25 mg/mL
ethanol (95%): 10% v/v
polyethylene glycol 400: 40% v/v
benzyl alcohol: 1.5% v/v
water: 48.5% v/v

What we claim is:

1. A pharmaceutical composition comprising an aqueous solution of from 0.1–8 mg/mL metolazone, 5–15% w/v ethanol (95%), 0–3% v/v benzyl alcohol and a cosolvent selected from 30–65% w/v propylene glycol, 25–50% v/v polyethylene glycol 300 or 25–50% v/v polyethylene glycol 400.

2. A pharmaceutical composition according to claim 1 wherein metolazone is present at a concentration of from 0.25 to 5 mg/mL.

3. A pharmaceutical composition according to claim 1 wherein ethanol (95%) is present at a concentration of from 5–10% w/v.

4. A pharmaceutical composition according to claim 1 wherein propylene glycol is present at a concentration of from 30–50% w/v.

5. A pharmaceutical composition according to claim 1 wherein polyethylene glycol 300 is present at a concentration of from 35–50% v/v.

6. A pharmaceutical composition according to claim 1 wherein polyethylene glycol 400 is present at a concentration of from 35–50% v/v.

7. A pharmaceutical composition according to claim 1 wherein benzyl alcohol is present at a concentration of from 1–2% v/v.

8. A pharmaceutical composition according to claim 1 wherein metolazone is present at a concentration of 0.5 mg/mL.

* * * * *

UNITED STATES PATENT AND TRADEMARK OFFICE
CERTIFICATE OF CORRECTION

Patent No.   : 5,124,152
Dated        : June 23, 1992
Inventor(s)  : Jennifer M. Biringer, et al

It is certified that error appears in the above-identified patent and that said Letters Patent is hereby corrected as shown below:

ABSTRACT

There are described pharmaceutical compositions comprising aqueous solutions of 7-chloro-1,2,3,4-tetrahydro-2-methyl-3-(2-methylphenyl)-4-oxo-6-quinazolinesulfonamide, ethanol and a cosolvent selected from propylene glycol or polyethylene glycols suitable for parenteral administration to a patient suffering form refractory edema.

Signed and Sealed this

Sixth Day of February, 1996

Attest:

BRUCE LEHMAN

*Attesting Officer*   Commissioner of Patents and Trademarks